(12) United States Patent
Rout et al.

(10) Patent No.: US 10,828,017 B2
(45) Date of Patent: Nov. 10, 2020

(54) SURGICAL INSTRUMENTS WITH MULTIPLE DEGREES OF FREEDOM AND METHODS OF USING THE SAME

(71) Applicant: Indian Institute of Technology Bombay, Mumbai (IN)

(72) Inventors: Sritam Rout, Mumbai (IN); Suresh Deshpande, Mumbai (IN); Ravi Bhallamudi, Mumbai (IN); Rupesh Ghyar, Mumbai (IN)

(73) Assignee: Indian Institute of Technology, Bombay, Mumbai (IN)

(*) Notice: Subject to any disclaimer, the term of this patent is extended or adjusted under 35 U.S.C. 154(b) by 168 days.

(21) Appl. No.: 15/727,622

(22) Filed: Oct. 8, 2017

(65) Prior Publication Data

US 2018/0064431 A1 Mar. 8, 2018

Related U.S. Application Data (63) Continuation of application No. PCT/IN2016/000093, filed on Apr. 11, 2016.

(30) Foreign Application Priority Data

Apr. 8, 2015 (IN) .......................... 1463/MUM/2015

(51) Int. Cl.
*A61B 17/00* (2006.01)
*A61B 17/29* (2006.01)
(Continued)

(52) U.S. Cl.
CPC ...... *A61B 17/00234* (2013.01); *A61B 1/3132* (2013.01); *A61B 17/29* (2013.01);
(Continued)

(58) Field of Classification Search
CPC .............. A61B 17/00234; A61B 17/29; A61B 17/2909; A61B 17/3201; A61B 1/3132;
(Continued)

(56) References Cited

U.S. PATENT DOCUMENTS 5,849,022 A * 12/1998 Sakashita ............... A61B 17/29
606/174
2005/0075664 A1 4/2005 Nagase et al.
2012/0226266 A1* 9/2012 Ghosal ................... A61B 17/29
606/1

FOREIGN PATENT DOCUMENTS

CN 101011292 8/2007
CN 203089228 7/2013
(Continued)

OTHER PUBLICATIONS

WIPO, Written Opinion in corresponding PCT Application PCT/IN2016/000093, dated Aug. 29, 2016.
(Continued)

*Primary Examiner* — Kathleen S Holwerda
*Assistant Examiner* — Brooke Labranche
(74) *Attorney, Agent, or Firm* — Ryan Alley IP (57) ABSTRACT

Surgical instruments are movable in several different dimensions and about several distinct axes. Surgical instruments include a head portion having a desired tool, a body portion freely moveable in several dimensions with respect to the head to which it connects via a connection or joint, which may be maneuverable and lockable in several head-body orientations. The connection may include one or more cooperative shafts, a rotator that angularly moves the head portion, a joint that translates the angular motion from rotator to the head in any relative orientation of the head portion, a crank that couples the shafts with the head portion, and a collar having an end slot to accommodate one or more (Continued)

of the shafts. In this way, as the shaft moves upward and downward, the head portion is transverse angularly displaced.

15 Claims, 6 Drawing Sheets

(51) Int. Cl.
    *A61B 17/3201*    (2006.01)
    *A61B 34/00*      (2016.01)
    *A61B 1/313*      (2006.01)
    *A61B 34/30*      (2016.01)
    *A61B 90/50*      (2016.01)

(52) U.S. Cl.
    CPC .......... *A61B 17/3201* (2013.01); *A61B 34/74* (2016.02); *A61B 17/2909* (2013.01); *A61B 34/25* (2016.02); *A61B 34/76* (2016.02); *A61B 90/50* (2016.02); *A61B 2017/00473* (2013.01); *A61B 2017/2927* (2013.01); *A61B 2017/2946* (2013.01); *A61B 2034/305* (2016.02)

(58) Field of Classification Search
    CPC .. A61B 2017/00473; A61B 2017/2927; A61B 2017/2946; A61B 2034/305; A61B 34/25; A61B 34/74; A61B 34/76; A61B 90/50
    See application file for complete search history.

(56) References Cited

FOREIGN PATENT DOCUMENTS

| | | | |
|---|---|---|---|
| CN | 103845112 | | 6/2014 |
| CN | 103845112 A | * | 6/2014 |
| CN | 104352264 | | 2/2015 |

OTHER PUBLICATIONS

WIPO, International Search Report in corresponding PCT Application PCT/IN2016/000093, dated Aug. 29, 2016.

* cited by examiner

SURGICAL INSTRUMENTS WITH MULTIPLE DEGREES OF FREEDOM AND METHODS OF USING THE SAME

RELATED APPLICATIONS

This application claims priority under 35 U.S.C. § 120 to, and is a continuation of, co-pending International Application PCT/IN2016/000093, filed Apr. 11, 2016 and designating the US, which claims priority to Indian Application 1463/MUM/2015, filed Apr. 8, 2015, such Indian Application also being claimed priority to under 35 U.S.C. § 119. These Indian and International applications are incorporated by reference herein in their entireties.

BACKGROUND

Laparoscopic or 'minimally invasive' surgery is a complex surgical technique where the surgery is performed through small incisions (usually 0.5-1 cm). Instruments are designed to safely manipulate delicate abdominal tissue during laparoscopic procedures. In general, a laparoscopic surgical instrument includes an elongated shaft carrying an end effector (or 'working end' or a 'head' portion) at its operative distal end and a handle or actuator or controller at its operative proximal end. The end effector can assume various forms, such as scissors, graspers, needle holders, dissectors, clamps, and the like.

SUMMARY

Example embodiments include surgical instruments movable in several different dimensions and about several distinct axes. Instruments include a head portion having a desired tool, a body portion freely moveable in several dimensions with respect to the head to which it connects via a connection or joint, which may be maneuverable and lockable in several head-body orientations. The connection may include one or more cooperative shafts, a rotator that angularly moves the head portion, a joint that translates the angular motion from rotator to the head in any relative orientation of the head portion, a crank that couples the shafts with the head portion, and a collar having an end slot to accommodate one or more of the shafts. In this way, as the shaft moves upward and downward, the head portion is transverse angularly displaced.

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the example embodiments herein.

DETAILED DESCRIPTION

Because this is a patent document, general broad rules of construction should be applied when reading it. Everything described and shown in this document is an example of subject matter falling within the scope of the claims, appended below. Any specific structural and functional details disclosed herein are merely for purposes of describing how to make and use examples. Several different embodiments and methods not specifically disclosed herein may fall within the claim scope; as such, the claims may be embodied in many alternate forms and should not be construed as limited to only examples set forth herein.

It will be understood that, although the terms first, second, etc. may be used herein to describe various elements, these elements should not be limited to any order by these terms. These terms are used only to distinguish one element from another; where there are "second" or higher ordinals, there merely must be that many number of elements, without necessarily any difference or other relationship. For example, a first element could be termed a second element, and, similarly, a second element could be termed a first element, without departing from the scope of example embodiments or methods. As used herein, the term "and/or" includes all combinations of one or more of the associated listed items. The use of "etc." is defined as "et cetera" and indicates the inclusion of all other elements belonging to the same group of the preceding items, in any "and/or" combination(s).

It will be understood that when an element is referred to as being "connected," "coupled," "mated," "attached," "fixed," etc. to another element, it can be directly connected to the other element, or intervening elements may be present. In contrast, when an element is referred to as being "directly connected," "directly coupled," etc. to another element, there are no intervening elements present. Other words used to describe the relationship between elements should be interpreted in a like fashion (e.g., "between" versus "directly between," "adjacent" versus "directly adjacent," etc.). Similarly, a term such as "communicatively connected" includes all variations of information exchange and routing between two electronic devices, including intermediary devices, networks, etc., connected wirelessly or not.

As used herein, the singular forms "a," "an," and "the" are intended to include both the singular and plural forms, unless the language explicitly indicates otherwise. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

The structures and operations discussed below may occur out of the order described and/or noted in the FIGs. For example, two operations and/or FIGs shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

The Inventors have newly recognized that laparoscopic instruments need to have a certain degree of maneuverability once inside the body cavity. Without adequate maneuverability, the instruments might cause damage to the internal tissue. However, maneuverability is limited due to restrictions in degrees of freedom of the instruments due to a small port of entry that is used to facilitate entry of the instruments. This inflexibility limits dexterous manipulation of the tissues. Furthermore, beyond the scope of laparoscopic surgeries, there is a requirement where a surgeon required angled entry into a bone or an organ. In at least one exemplary scenario, a surgeon may be required to enter and view an organ or a body part or its interiors by using a scope in a variety of views. In other words, the surgeon may require a scope head to be manipulated in multiple degrees of freedom. In at least one other exemplary scenario, a surgeon may be required to enter a bone at an angle or enter linearly and then change angle inside the bone or to drill a hole in a bone which is not linear. All these require a scope head to be manipulated in multiple degrees of freedom.

Many existing devices use a system of wires, joints, flexible components and pulleys—in order to achieve the required maneuverability. However, these wires are delicate and their use involves a large number of moving parts which may cause failure during use. Also, the use of complicated parts limits the reusability of those devices. The connecting wires might slack after repeated sterilization which leads to imperfect force transfer from a surgeon's hand to the end effector. Therefore, there a need to provide an instrument that not only addresses problems of limited maneuverability, but also overcomes problems relating to complexity and reusability. To overcome these newly-recognized problems as well as others and achieve these advantages, the inventors have developed example embodiments and methods described below to address these and other problems recognized by the Inventors with unique solutions enabled by example embodiments.

The present invention is surgical instruments with multiple degrees of freedom and methods of using the same. In contrast to the present invention, the few example embodiments and example methods discussed below illustrate just a subset of the variety of different configurations that can be used as and/or in connection with the present invention.

Example embodiments include apparatuses which facilitates the required degrees of freedom in an instrument. The major components of the device include a distal tool head, a proximal handle and a central system to achieve the required maneuverability. The instrument can be modified to be used as a scissor, grasper, tissue retractor, stapler, or the like.

Figure 1:
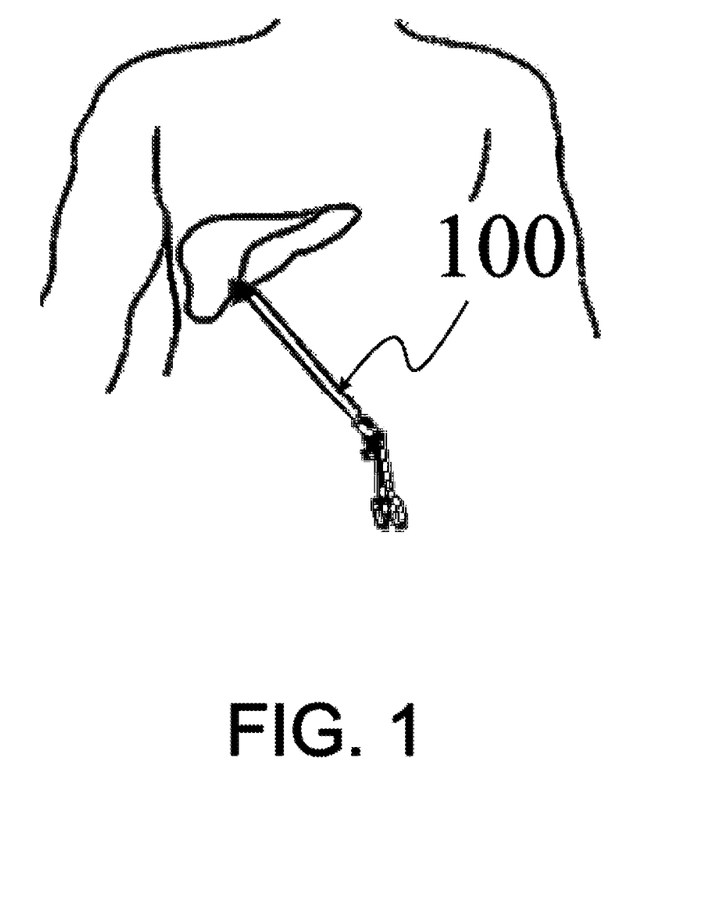
FIG. 1 illustrates is a perspective view of the instrument with an illustrious view of patient's body.

FIG. 1 illustrates is a perspective view of the instrument 100 with an illustrious view of patient's body. In accordance with an example embodiment, there is provided a body portion 4, 5 and a head portion 1, 2 for the instrument. A central system 3 connects the body portion to the head portion. Typically, the body portion forms a channel for transmission of force and motion from an operative proximal end to an operative distal end of the instrument. Typically, the head portion is an end effector which comprises a working apparatus or a tool head 1 in accordance with the reason for which the instrument is designed. In other words, the end effector, in at least one embodiment, may comprise a grasper; in another embodiment, may comprise a pair of scissors; in yet another embodiment, may comprise a stapler, in still another embodiment, may comprise a scope, in another embodiment, may comprise a drill; and the like. Typically, the head portion is spaced apart from the body part. This spaced apart provision provides for multiple degrees of freedom of the head portion, effected by the body portion. This working apparatus of tool head is controlled by an operatively proximally located first trigger. Furthermore, this head portion (with tool head) can be moved and locked at any angle with respect to the body portion. The central system consists of a universal joint and a series of other parts which are linked to each other to achieve the required degrees of freedom in the instrument.

In accordance with another example embodiment, there is provided a first inner shaft 3c configured to provide actuation of apparatus which is located at operative distal end of the instrument. The apparatus, typically, is a part of the head portion, and is actuated from an operative proximal part of the instrument. Typically, a first trigger 4 is provided which provides for actuation of the apparatus of the head portion, which apparatus provides for the core action or utility or function of the instrument, as such. In at least a first embodiment, this first trigger is a handle with a stationary part and a moving part. In at least a second embodiment, this first trigger is an angularly displaceable knob with at least a cam which translates an angular displacement motion to a motion desired by the apparatus. In at least a third embodiment, this first trigger is a push button for an on-off function. The first trigger is operatively proximally located for use by a user. In at least one embodiment, the first trigger has a fixed part 4a and a moving part 4b, which effectively transfers motion to the parts of the tool head 1, 2

In accordance with yet another example embodiment, there is provided a second middle shaft 3b configured to provide a first set of degrees of freedom for the operative distal end of the instrument. Typically, the second middle shaft is co-axial to and outside the first inner shaft. Typically, the second middle shaft is configured to provide angular displacement of the head portion, and therefore the operatively distally located end effector.

In accordance with still another example embodiment, there is provided a third outer shaft 3a configured to provide a cover and support for actuating assemblies or motion translators from the first inner shaft and from the second middle shaft. Typically, the third outer shaft is co-axial to and outside the second middle shaft. The third outer shaft is connected to the head portion by a hinged link which allows for transverse angular displacement of the head portion with respect to the body portion but restricts its medial lateral displacement.

In accordance with an additional example embodiment, there is provided a rotator 4c at an operative distal end of the instrument. Rotator 4c is communicably coupled to the first inner shaft. As rotator 4c is angularly displaced by a user, about its axis, the communicably coupled first inner shaft angularly displaces about its axis, and therefore, the apparatus located at the operative distal end also angularly displaced about its axis. Typically, a universal joint 3d is provided, at the operative distal end of the body portion, and ensconced with the third outer shaft, such that, it translates angular displacement of rotator 4c to the head portion irrespective of its transversely angularly displacement position with respect to the body portion.

In accordance with another additional example embodiment, there is provided a crank configured to communicably couple the second middle shaft with the head portion. In at least one embodiment, the crank is a series of links starting from the second middle shaft 3b and hinged to the head portion. A second trigger 4d is provided such that its actuation motion is translated in to an operative forward and rearward motion of the second middle shaft. In at least one embodiment, the second trigger is a stub with a cam, which stub is angularly displaceable, and which stub is disposed in a cantilever manner from the second middle shaft, which can be used by a user with the help of a single finger even while two fingers or the hand operate or rest at the first trigger. The second trigger is operatively proximally located for use by a user. A lock 4e is provided in order to lock the crank.

In at least one embodiment, a collar with a pre-defined slot is provided at the operative distal end of the second middle shaft in the body portion so that a corresponding second head portion located middle shaft moves operatively upward and downward, thereby causing transverse angular displacement of the entire head portion with the apparatus. In at least one embodiment, the pre-defined slot is a linear operatively transverse slot such that the corresponding second head portion located middle shaft moves operatively upward and downward at its one end which is located inside the slot.

Figure 2:
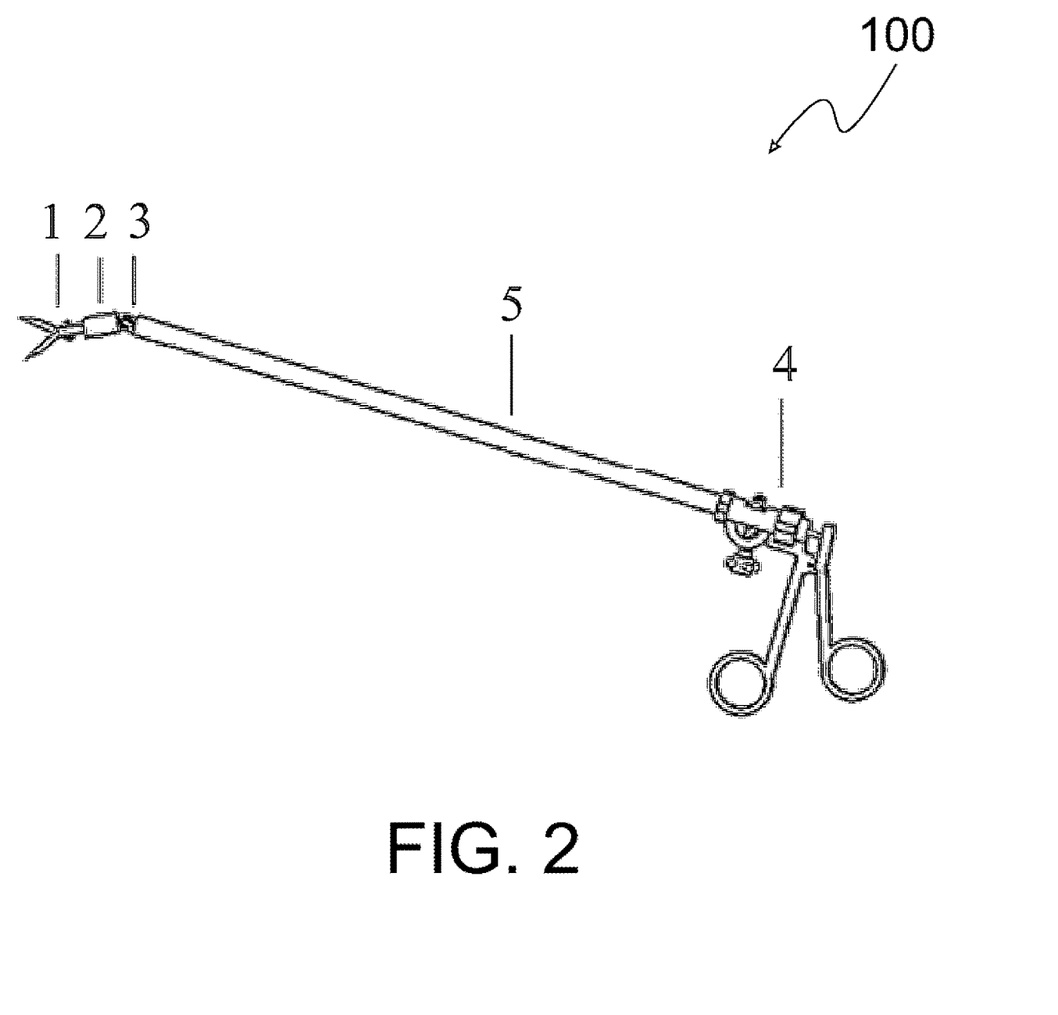
FIG. 2 illustrates an enlarged view of the instrument showing the essential working parts of the device.

FIG. 2 illustrates an enlarged view of the instrument showing the essential working parts of the device. The instrument, typically, consists of an operative distal tool/end effector (head portion) 1 which is controlled by an operative proximally located handle or first trigger 4, and a central system 3 connecting the tool head 2 and an operative proximal handle 4 through a series of links, to achieve required maneuverability. The functionality of the central system 3 is also controlled by various embodiments in the operative proximal handle 4.

Figure 3:
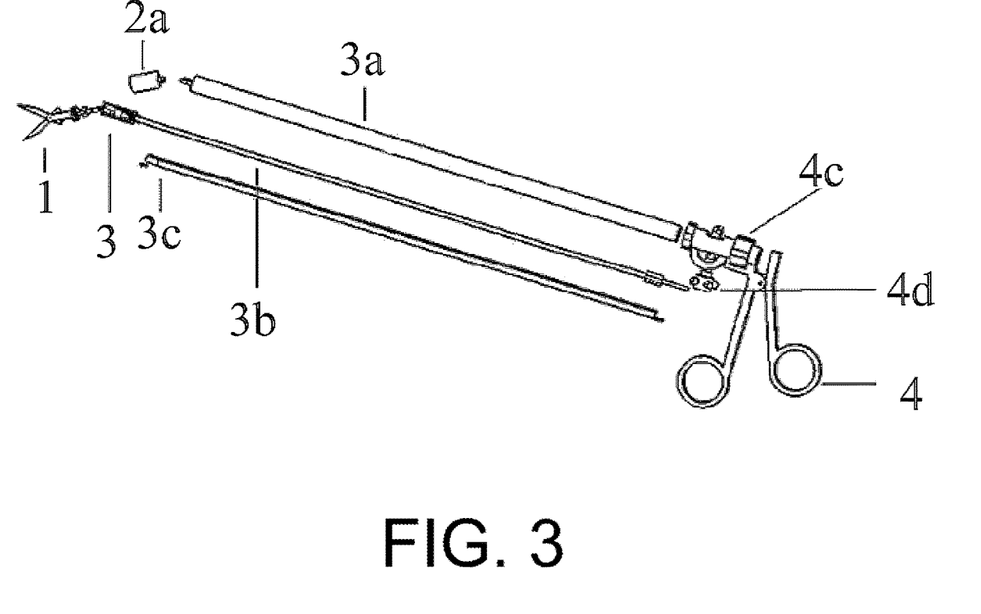
FIG. 3 illustrates an exploded view of the entire device.
Figure 4A:
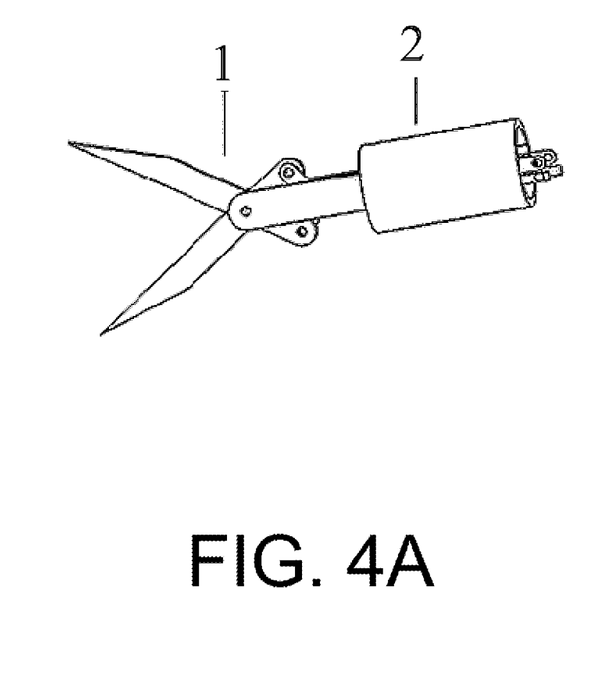
FIG. 4A illustrates a perspective view of the distal tool head and a tool/end effector.

FIG. 3 illustrates an exploded view of the entire device. FIG. 4A illustrates a perspective view of the distal tool head and a tool/end effector. The perspective view of the distal tool head 2 consists of the tool assembly 1a, 1b, 1c, 1d connected to the tool head 2. The tool assembly 1a, 1b, 1c, 1d shown in the figure is a scissor assembly according to one embodiment. For the purposes of this specification, the tool assembly 1 may be referred to as a scissor assembly and vice versa.

Figure 4B:
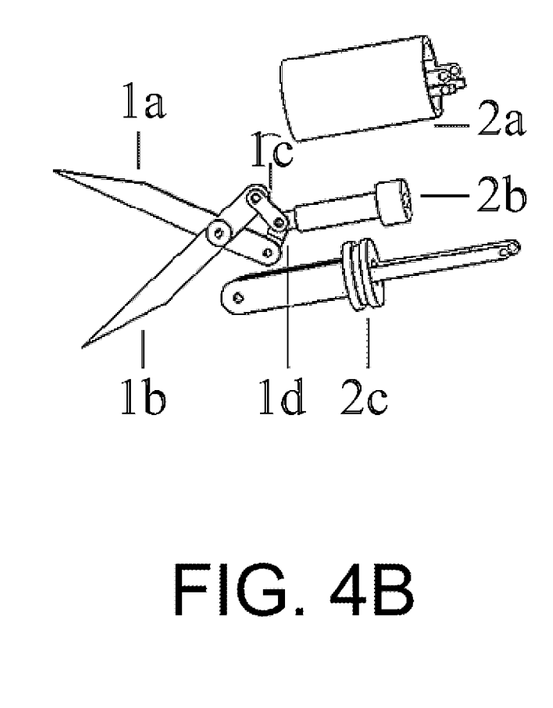
FIG. 4B illustrates an exploded view of the distal tool head and a tool/end effector.

FIG. 4B illustrates an exploded view of the distal tool head and a tool/end effector. The exploded view of the tool head 2 and tool assembly 1 consists of two scissor jaws 1a, 1b connected to a rigid cylindrical rod 2b via links 1c, 1d. It also shows a front rotating collar 2c and the front cover 2a.

Figure 5A:
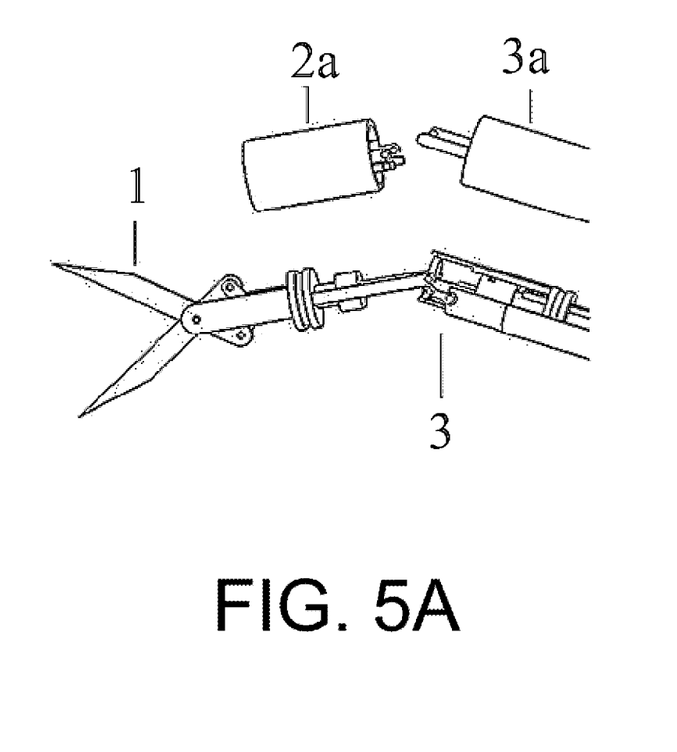
FIG. 5A illustrates a perspective view of the central system.

FIG. 5A illustrates a perspective view of the central system. This figure features the central assembly 3 which has been designed to achieve the required maneuverability. It also shows a front cover 2a and a third outer shaft 3a.

Figure 5B:
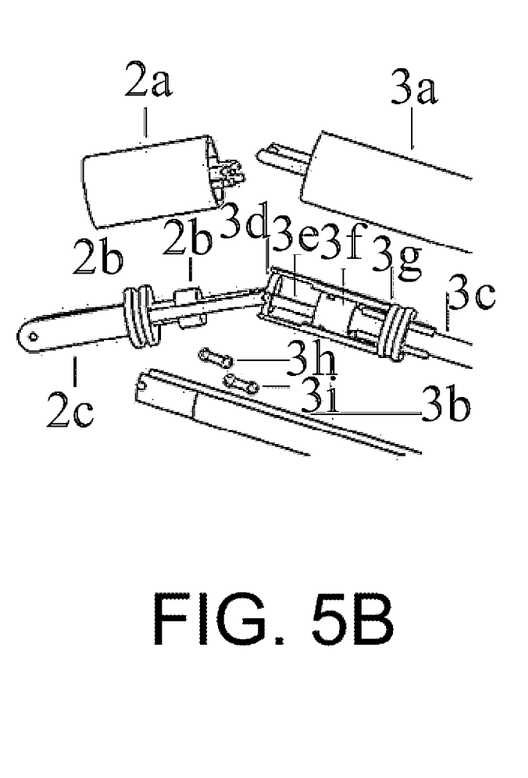
FIG. 5B illustrates an exploded view of the central system.

FIG. 5B illustrates an exploded view of the central system. This figure shows a detailed view of the central assembly 3. It has a back rotating collar 3g connected to the front rotating collar 2c via a universal joint 3d. It also shows a slider-crank system consisting of the rigid cylindrical rod 2b and, a rigid slider 3e sliding on a cylinder 3f. The cylinder 3f is connected to a first inner shaft 3c which is disposed within the back rotating collar 3g. The figure also shows a second middle shaft 3b and two rigid links 3h, 3i.

Figure 6A:
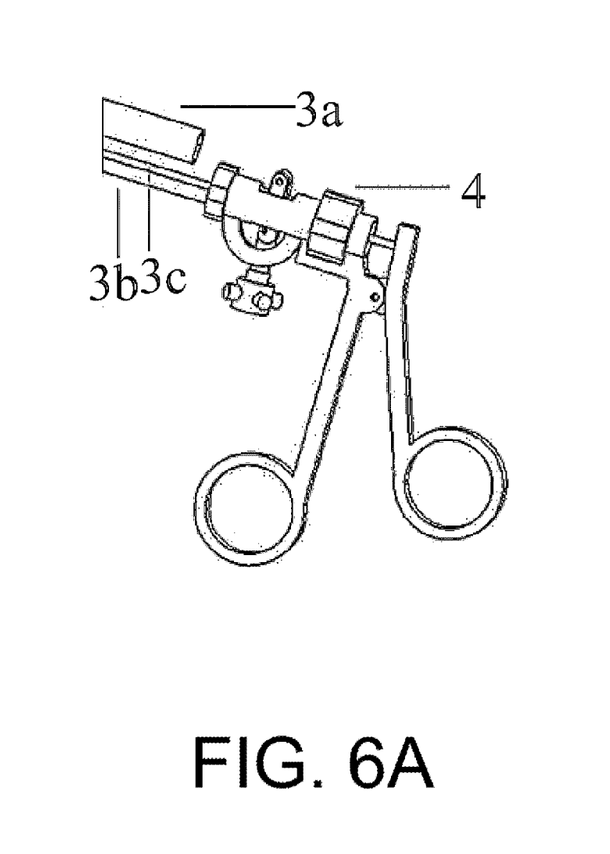
FIG. 6A illustrates a perspective view of the proximal handle.
Figure 6B:
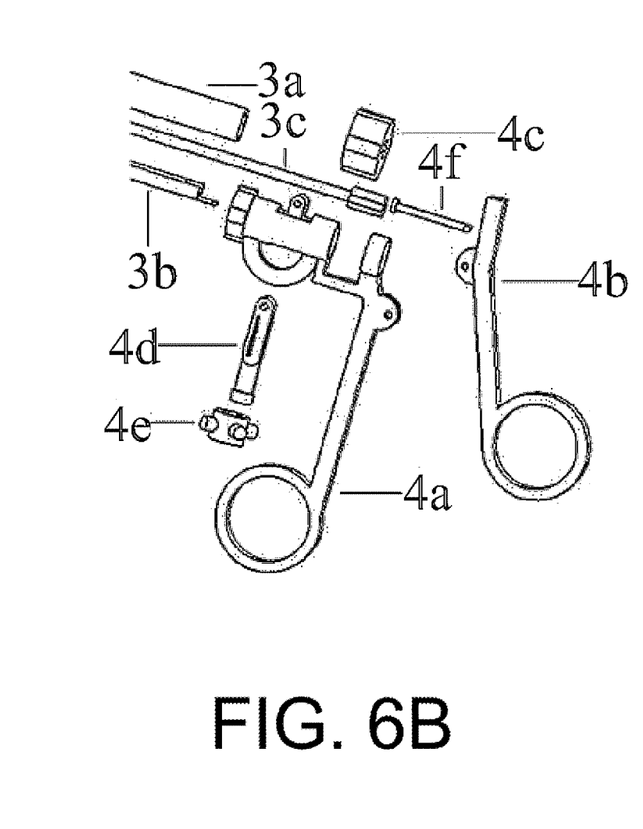
FIG. 6B illustrates an exploded view of the proximal handle.

In effect, the central system is configured to provide the following functions:
  angular displacement of the head portion, in an angled position
  actuation of distal tool head of the head portion, in an angled position
  transverse angular displacement of the head portion with respect to the body portion FIG. 6A illustrates a perspective view of the proximal handle. This figure shows the handle assembly 4 connected to the third inner shaft 3c and to the second middle shaft 3b. FIG. 6B illustrates an exploded view of the proximal handle. This figure shows an exploded view of the handle assembly 4. It consists of the fixed part of the handle 4a, a tool manipulator 4b, a rotator 4c, a maneuvering trigger 4d with a locking mechanism such as locknut 4e and a connector 4f. Typically, this connector 4e is a cylindrical connector. This figure shows the joints and links between the first inner shaft 3c and the hollow semi-cylinder 3b with the handle assembly 4.

The movement of the tool manipulator 4b of the first trigger 4 controls the actuation of the tool assembly 1 [opening and closing of the jaws of the tool assembly 1]. The angular displacement of the tool head 2 in the transverse direction to the longitudinal axis is controlled by the second trigger 4d [maneuvering trigger 4d]. The tool head 2 can be locked at any angle in the transverse direction by the locknut 4e. The axial angular displacement of the tool assembly 1 is controlled by the rotator 4c.

The motion of the tool manipulator 4b is transferred to the tool assembly 1 via a series of links. As, shown in FIG. 6A, the tool manipulator 4b is connected to the fixed part of the handle 4a via a hinge joint. As shown in FIG. 4B, in at least one embodiment, the opening and closing of the jaws 1a, 1b of the tool assembly 1 is accomplished by a simple scissor mechanism. As shown in FIG. 5B, the scissor jaws 1a, 1b are controlled by the operative forward and operative backward movement of the rigid cylindrical rod 2b disposed within the front rotating collar 2c. The rigid rod 2b is connected to a slider 3e that slides freely in the transverse direction on a cylinder 3f. The cylinder 3f is connected to the first inner shaft 3c (FIG. 5B) via a cylindrical joint. The first inner shaft 3c passes centrally through the back rotating collar 3g and can slide freely on it. Grooves on the first inner shaft 3c ensure simultaneous angular displacement of the first inner shaft 3c and the back rotating collar 3g (FIG. 5B). As shown in FIG. 6B, the proximal end of the first inner shaft 3c is connected to the distal end of the cylindrical connector 4f. The proximal end of the cylindrical connector 4f is connected to the tool manipulator 4b. The hinge between proximal end of the rigid rod 2b and distal end of the slider 3e ensures unrestricted angular displacement of the tool head 2 in the transverse direction to the longitudinal axis. The series of joints described above ensure tool manipulation even at a transverse angle of the tool head 2 via a slide-crank (FIG. 5B).

The tool head 2 angular displacement in a transverse direction to the longitudinal axis is accomplished by a semi-cylindrical rod 3b, typically hollow, which is disposed centrally within the third outer shaft 3a and slides freely on it (FIG. 5A). The distal portion of the second middle shaft 3b is connected to the tool head 2 via rigid links 3h, 3i and its proximal end is connected to the maneuvering trigger 4d. The maneuvering trigger 4d is connected to the fixed part of the handle 4a via a hinge joint. The forward and backward motion of the maneuvering trigger 4d manipulates the tool head 2 though a crank. The tool head 2 can be locked at any desired angle by the locknut 4e.

The axial rotation of the tool assembly 1 is controlled by the rotator 4c. As shown in FIG. 6B, the distal end of the first inner shaft 3c is connected to the rotator 4c via a groove such that it can slide inside the rotator 4c and both the embodiments angularly displace together. When the rotator 4c is angularly displaced, it turns the first inner shaft 3c, which in turn angularly displaces the back rotating collar 3g by a similar principle (FIG. 5B). The back rotating collar 3g angularly displaces the front rotating collar 2c because of the universal joint 3d (FIG. 5B). The front collar 2c angularly displaces relative to the front cover 2a because of a cylindrical joint between them. Similarly, the back rotating collar 3g also angularly displaces relative to the back cover 3a. As shown in FIG. 5A, the tool assembly 1 is connected to the front rotating collar 2c via a pivot-hinge type joint such that the axial rotation of the collar 2c angularly displaces the tool assembly 1 in the axial direction.

As shown in FIG. 5A, the distal part of the back cover 3a and the proximal part of the front cover 2a are connected via a hinge joint. The proximal part of the back cover 3a is locked to the fixed part of the handle 4a.

Example embodiments may provide surgical instruments having movement beyond 2 degrees of freedom. In fact, due to its dual body system, it provides for at least 7 degrees of freedom in a manner such that transmission of force is accurate and provides dexterity to a surgeon using this instrument. Moreover, the technical design is such that wires, flexible rods, flat bands, and the like (which were previously used for maneuverability) are eliminated, thereby providing reliability of use, in an accurate manner, even after repeated sterilization procedures. Furthermore, even in angled positions or in angularly displacement positions, a surgeon can use this instrument.

Example methods and embodiments thus being described, it will be appreciated by one skilled in the art that example embodiments may be varied through routine experimentation and without further inventive activity. For example, example embodiments have been described with respect to certain surgical tools at an end of an instrument, it is understood that any type of vastly different surgical implements, with further-extending portions, may be used in the same. Variations are not to be regarded as departure from the spirit and scope of the exemplary embodiments, and all such modifications as would be obvious to one skilled in the art are intended to be included within the scope of the following claims.

What is claimed is:

1. A surgical instrument with multiple degrees of freedom, the instrument comprising:
    a head portion including a distal tool head;
    a body portion spaced apart from the head portion by a space providing for multiple degrees of freedom of the head portion; and
    a central system configured to connect the head portion to the body portion and further configured to achieve maneuverability and locking ability to the head portion in multiple degrees of freedom, wherein the central system includes,
        an assembly of shafts, wherein the assembly of shafts includes a first inner shaft, a second middle shaft co-axial and outer to the first inner shaft, and a third outer shaft co-axial and outer to the second middle shaft,
        a rotator configured to angularly displace the head portion,
        a universal joint configured to translate angular displacement of the rotator to the head portion irrespective of its transversely angularly displacement position with respect to the body portion,
        a crank including a rigid cylindrical rod and rigid slider sliding on a cylinder, wherein the cylinder is connected to a central rod disposed within a back rotating collar, and wherein the crank communicably couples the assembly of shafts with the head portion, and
        a collar with a slot at an operative distal end of at least one of the shafts so that as the one shaft moves upward and downward, the head portion is transversely angularly displaced, wherein the slot of the collar is a linear operatively transverse slot such that the second middle shaft moves upward and downward at one end inside the slot.

2. The surgical instrument of claim 1, wherein the crank is configured to communicably couple the second middle shaft with the head portion.

3. The surgical instrument of claim 1, wherein the at least one of the shafts is the second middle shaft.

4. The surgical instrument of claim 1, further comprising:
    a first trigger configured to provide actuation of the tool head, wherein the first trigger is a handle with a stationary part and a moving part.

5. The surgical instrument of claim 1, further comprising:
    a first trigger configured to provide actuation of the tool head, wherein the first trigger is an angularly-displaceable knob with a cam that translates an angular displacement motion to a motion of the tool head.

6. The surgical instrument of claim 1, further comprising:
    a first trigger configured to actuate the tool head, wherein the first trigger is a push button for an on-off function.

7. The surgical instrument of claim 1, wherein the rotator is communicably coupled to the first inner shaft, wherein the rotator is angularly displaceable about a longitudinal axis of the rotator so as to angularly displace the communicably coupled first inner shaft about a longitudinal axis of the first inner shaft and angularly displace the distal tool head about a longitudinal axis of the distal tool head.

8. The surgical instrument of claim 1, wherein the universal joint is at the operative distal end of the body portion and ensconced with the third outer shaft so that the third outer shaft translates angular displacement of the rotator to the head portion irrespective of its transverse angular displacement position with respect to the body portion.

9. The surgical instrument of claim 1, wherein the crank is a series of links starting from the second middle shaft and hinged to the head portion.

10. The surgical instrument of claim 1, further comprising:
    a second trigger configured to provide actuation of the second middle shaft, wherein the second trigger is a stub with a cam, wherein the stub is angularly displaceable and cantilevered from the second middle shaft.

11. The surgical instrument of claim 1, further comprising:
    a second trigger configured to provide actuation of the second middle shaft, wherein the second trigger is provided with a lock.

12. The surgical instrument of claim 1, wherein the back rotating collar is connected to a front rotating collar via the universal joint.

13. The surgical instrument of claim 1, wherein the central system includes two rigid links.

14. The surgical instrument of claim 1, wherein the tool head is one or more of a grasper, a pair of scissors, a stapler, a scope, a drill, a tissue retractor, a cauterizing mechanism, and a sterilizing mechanism.

15. A surgical instrument with multiple degrees of freedom, the instrument comprising:
- a head portion including a distal tool head;
- a body portion spaced apart from the head portion by a space providing for multiple degrees of freedom of the head portion;
- a central system configured to connect the head portion to the body portion and further configured to achieve maneuverability and locking ability to the head portion in multiple degrees of freedom, wherein the central system includes,
  - an assembly of shafts,
  - a rotator configured to angularly displace the head portion,
  - a universal joint configured to translate angular displacement of the rotator to the head portion irrespective of its transversely angularly displacement position with respect to the body portion,
  - a crank including a rigid cylindrical rod and rigid slider sliding on a cylinder, wherein the cylinder is connected to a central rod disposed within a back rotating collar, and wherein the crank communicably couples the assembly of shafts with the head portion, and
  - a collar with a slot at an operative distal end of at least one of the shafts so that as the one shaft moves upward and downward, the head portion is transversely angularly displaced;
- a first inner shaft configured to provide actuation of the tool head;
- a first trigger configured to provided actuation of the tool head;
- a second middle shaft configured to provide a first set of degrees of freedom for the head portion, wherein the second middle shaft is co-axial to and outside the first inner shaft, and wherein the second middle shaft is configured to provide angular displacement to the head portion;
- a third outer shaft configured to provide support for an actuator or motion translator from the first inner shaft and from the second middle shaft, wherein the third outer shaft is co-axial to and outside the second middle shaft, wherein the third outer shaft is connected to the head portion by a hinged link permitting transverse angular displacement of the head portion with respect to the body portion restricting its medial-lateral displacement; and
- a second trigger having actuation motion that translates to an operative forward and rearward motion of the second middle shaft.

* * * * *